United States Patent
Thomas et al.

(10) Patent No.: US 12,394,049 B2
(45) Date of Patent: Aug. 19, 2025

(54) METHOD AND SYSTEM FOR DATA EXTRACTION FROM ECHOCARDIOGRAPHIC STRAIN GRAPHS

(71) Applicant: Northwestern University, Evanston, IL (US)

(72) Inventors: James David Thomas, Evanston, IL (US); Rahul Anand Devathu, Evanston, IL (US); Ramsey Michael Wehbe, Evanston, IL (US)

(73) Assignee: Northwestern University, Evanston, IL (US)

( * ) Notice: Subject to any disclaimer, the term of this patent is extended or adjusted under 35 U.S.C. 154(b) by 550 days.

(21) Appl. No.: 17/986,504

(22) Filed: Nov. 14, 2022

(65) Prior Publication Data

US 2023/0153997 A1  May 18, 2023

Related U.S. Application Data

(60) Provisional application No. 63/278,708, filed on Nov. 12, 2021.

(51) Int. Cl.
| | |
|---|---|
| *G06F 17/00* | (2019.01) |
| *A61B 8/08* | (2006.01) |
| *G06T 7/00* | (2017.01) |

(52) U.S. Cl.
CPC .......... *G06T 7/0012* (2013.01); *A61B 8/0883* (2013.01); *G06T 2207/30048* (2013.01)

(58) Field of Classification Search
CPC .............................. G06T 7/0012; A61B 8/0883
See application file for complete search history.

(56) References Cited

U.S. PATENT DOCUMENTS

| | | | |
|---|---|---|---|
| 8,626,279 B2* | 1/2014 | Edvardsen | A61B 5/349 600/515 |
| 11,763,456 B2* | 9/2023 | Meyers | G06T 7/37 382/103 |
| 11,810,303 B2* | 11/2023 | Meyers | G06T 7/90 |
| 12,133,762 B2* | 11/2024 | Klingensmith | G06T 7/75 |
| 12,288,338 B2* | 4/2025 | Seo | G06T 7/0012 |

(Continued)

OTHER PUBLICATIONS

Phelan D, Collier P, Thavendiranathan P, et al., "Relative apical sparing of longitudinal strain using two-dimensional speckle-tracking echocardiography is both sensitive and specific for the diagnosis of cardiac amyloidosis," *Heart* 2012; 98:1442-1448. (Doi: 10.1136/heartjnl-2012-302353. Epub Aug. 3, 2012).

(Continued)

*Primary Examiner* — Mohammed H Zuberi
(74) *Attorney, Agent, or Firm* — Bell & Manning, LLC

(57) ABSTRACT

A system to analyze heart data includes a memory configured to store echocardiographic strain image data. The system also includes a processor operatively coupled to the memory and configured to segment the echocardiographic strain image data. The processor is also configured to analyze the segmented echocardiograph strain image data to generate a point cluster of pixels. The processor is also configured to stitch together points in the point cluster to generate a continuous curve that represents the echocardiographic strain image data. The processor is further configured to analyze the continuous curve to identify a heart condition.

16 Claims, 6 Drawing Sheets

(56) References Cited

U.S. PATENT DOCUMENTS

| | | | | |
|---|---|---|---|---|
| 2008/0081997 | A1* | 4/2008 | Kakihara | G06T 7/0012 702/19 |
| 2008/0221451 | A1* | 9/2008 | Kanda | A61B 8/08 600/453 |
| 2008/0285819 | A1* | 11/2008 | Konofagou | A61B 8/485 382/128 |
| 2010/0280355 | A1* | 11/2010 | Grimm | A61B 5/02028 600/437 |
| 2011/0081066 | A1* | 4/2011 | Jolly | G06T 7/174 382/131 |
| 2011/0092809 | A1* | 4/2011 | Nguyen | A61B 5/283 600/424 |
| 2011/0263996 | A1* | 10/2011 | Edvardsen | A61B 5/363 600/518 |
| 2013/0066211 | A1* | 3/2013 | Konofagou | G01S 7/52057 600/450 |
| 2014/0071125 | A1* | 3/2014 | Burlina | G06T 17/00 345/420 |
| 2016/0217572 | A1* | 7/2016 | Akahori | G06T 7/0014 |
| 2018/0280690 | A1* | 10/2018 | Kim | A61L 31/146 |
| 2019/0246913 | A1* | 8/2019 | Zaremba | A61B 8/0883 |
| 2019/0247016 | A1* | 8/2019 | Upton | G16H 50/30 |
| 2020/0160980 | A1* | 5/2020 | Lyman | G06F 18/217 |
| 2020/0297284 | A1* | 9/2020 | O'Brien | G16H 50/20 |

OTHER PUBLICATIONS

Kristina H. Haugaa et al., "Rick Assessment of Ventricular Arrhythmias in Patients with Nonischemic Dilated Cardiomyopathy by Strain Echocardiography," *Journal of the American Society of Echocardiography*, vol. 25, Issue 6, Jun. 2012; pp. 667-673.

Brainin, P. Myocardial Postsystolic Shortening and Early Systolic Lengthening: Current Status and Future Directions. *Diagnostics* 2021, 11, 1428. https://doi.org/10.3390/diagnostics11081428.

Mirea O, Vallecilla C, Claus P, Rademakers F, D'hooge J (2020) Experimental validation of the prestretch-strain relationship as a non-invasive index of left ventricular myocardial contractility. *PLoS One* 15(2): e0228027 https://doi.org/10.1371/journal.pone.0228027).

Partho P. Sengupta et al., "Cognitive Machine-Learning Algorithm for Cardiac Imaging A Pilot Study for Differentiating Constrictive Pericarditis From Restrictive Cardiomyopathy," *Circ Cardiovasc Imaging.* 2016; 9: e004330. DOI: 10.1161/CIRCIMAGING.115.004330.

Kristina H. Haugaa et al., "Strain Echocardiography Improves Risk Prediction of Ventricular Arrhythmias After Myocardial Infarction," *JACC: Cardiovascular Imaging*, vol. 6, No. 8, 2013; pp. 1-10. http://dx.doi.org/10.1016/j.jcmg.2013.03.005.

\* cited by examiner

METHOD AND SYSTEM FOR DATA EXTRACTION FROM ECHOCARDIOGRAPHIC STRAIN GRAPHS

CROSS-REFERENCE TO RELATED APPLICATION

The present application claims the priority benefit of U.S. Provisional Patent App. No. 63/278,708 filed on Nov. 12, 2021, the entire disclosure of which is incorporated herein by reference.

BACKGROUND

Echocardiography refers to a non-invasive and painless test that uses sound waves to create images of the heart. During such an echo test, ultrasound (high-frequency sound waves) from a hand-held wand are directed onto the chest of a patient, and are used to provide images of the valves and chambers of the heart. These images can be used by the physician to evaluate the pumping action of the heart. Additionally, echocardiographic strain imaging can be used for assessment of myocardial function/viability, detection of acute allograft rejection, etc.

SUMMARY

An illustrative system to analyze heart data includes a memory configured to store echocardiographic strain image data. The system also includes a processor operatively coupled to the memory and configured to segment the echocardiographic strain image data. The processor is also configured to analyze the segmented echocardiograph strain image data to generate a point cluster of pixels. The processor is also configured to stitch together points in the point cluster to generate a continuous curve that represents the echocardiographic strain image data. The processor is further configured to analyze the continuous curve to identify a heart condition.

In an illustrative embodiment, the echocardiographic strain image data includes one or more visual graphs depicting a plurality of apical echo views of a heart. Each of the apical echo views of the heart can contain a plurality of curves that are coded to specify locations within the heart. In one embodiment, the continuous curve is formed by use of an interpolated univariate spline on the point cluster. In another embodiment, segmentation of the echocardiographic strain image data extracts a scale and graph data from the echocardiographic strain image data.

In another embodiment, the processor is configured to convert the graph data into a two-dimensional array of hue saturation values, and also to identify all pixels in the graph data that represent a specific location of the heart. In an illustrative embodiment, the processor is configured to convert the identified pixels into the point cluster of pixels, where the point cluster is based on row and column indices of the identified pixels. In another embodiment, the processor analyzes the continuous curve to identify one or more patterns present in the echocardiographic strain image data. The processor can compare the one or more patterns to previously analyzed strain data to identify the heart condition. In one embodiment, the one or more patterns relate to a timing of peak strain in the echocardiograph strain image data. In another embodiment, the one or more patterns relate to early systolic lengthening and post systolic shortening. In another embodiment, the one or more patterns relate to myocardial stretch with atrial contraction.

An illustrative method of analyzing heart data includes storing, in a memory, echocardiographic strain image data. The method also includes segmenting, by a processor operatively coupled to the memory, the echocardiographic strain image data. The method also includes analyzing the segmented echocardiograph strain image data to generate a point cluster of pixels. The method also includes stitching together, by the processor, points in the point cluster to generate a continuous curve that represents at least a portion of the echocardiographic strain image data. The method further includes analyzing, by the processor, the continuous curve to identify a heart condition.

In an illustrative embodiment, the segmenting includes segmenting the echocardiographic strain image data into a scale and graph data. The method can also include converting, by the processor, the graph data into a two-dimensional array of hue saturation values. The method can also include identifying, by the processor, all pixels in the graph data that represent a specific location of the heart, and converting the identified pixels into the point cluster of pixels. The method can also include analyzing, by the processor, the continuous curve to identify one or more patterns present in the echocardiographic strain image data. The method can further include comparing, by the processor, the one or more patterns to previously analyzed strain data to identify the heart condition.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

One of the most important developments of the past 20 years in the field of echocardiography has been myocardial strain analysis, which is most commonly performed by frame-to-frame tracking of small "speckles" that can be seen using two-dimensional (2D) ultrasound imaging. This modality often serves as an early warning marker, as it turns abnormal prior to more conventional parameters of cardiac performance, such as left ventricular ejection fraction. Strain analysis can be used to detect subclinical cardiac dysfunction in diverse clinical conditions such as heart failure, cancer chemotherapy, valvular heart disease, coronary artery disease, pulmonary hypertension, and many others.

In traditional echo strain analysis, the obtained echo strain information is reduced to a single number, the global longitudinal strain (GLS), with normal values less than ~−17%. Unfortunately, this discards a huge amount of strain data reflecting the spatial and temporal distribution of strain. Studies have shown value in the spatial distribution of strain for detecting cardiac amyloidosis with the temporal pattern of strain showing predictive accuracy for life-threatening arrhythmias and cardiac constriction.

The inventors have thus hypothesized that the spatial-temporal strain curves that are output from strain analysis contain important subtleties that are relevant to clinical or research applications. For example, it has been shown that the timing of peak strain in the individual segments can predict ventricular tachycardia better than strain magnitude itself. Also, evidence of early systolic lengthening and post-systolic shortening can identify acute ischemia or myocardial stunning, but is entirely missed when only global strain is considered. Finally, it has recently been demonstrated that consideration of the myocardial stretch with atrial contraction (a feature entirely missed on routine strain imaging) adds important information concerning ventricular contractility. An experimental validation has been performed of the pre-stretch-strain relationship as a non-invasive index of left ventricular myocardial contractility. Thus, detecting the shape of the curves will add important additional information to routine strain analysis.

Unfortunately, the spatio-temporal strain analysis, while necessary to calculate global longitudinal strain, is rarely stored in a readily usable format. Rather, results of the spatio-temporal strain analysis are generally in the form of pictures/images of the output graphs. To exploit this lost spatio-temporal strain data, the proposed methods and systems aim firstly to extract the raw numerical data from the myriad of strain curve images stored in echo studies, and second, but crucially, use these data in statistical analysis and machine learning to further exploit the rich data that would otherwise be lost in traditional strain analysis.

Figure 1:
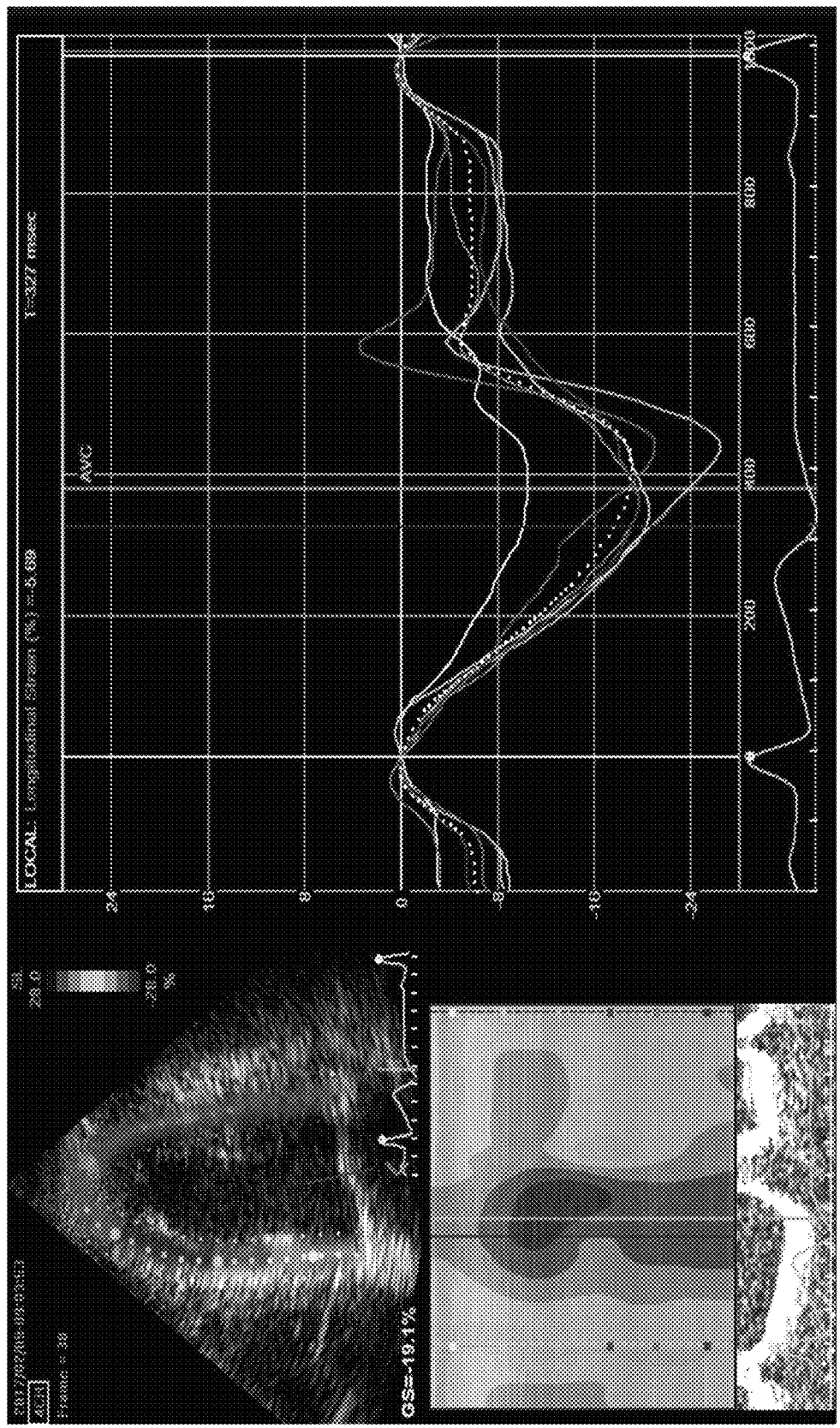
FIG. 1 depicts a visual graph with results of spatio-temporal strain analysis in accordance with an illustrative embodiment.

As a first stage of implementing the proposed system, the inventors have worked to expand access to retrospective strain databases. While temporal strain data can be exported as one-dimensional (1D) numerical datasets from vendor-specific and -neutral software packages, this process is not standardized, common, or easy. Instead, the temporal data is usually exported as visual graphs from the three apical echo views, each containing six curves, color coded to specify their location around the left ventricle. FIG. 1 depicts a visual graph with results of spatio-temporal strain analysis in accordance with an illustrative embodiment. The proposed method extracts these data using intelligent graph identification, optical character recognition, and curve conversion algorithms.

Figure 3:
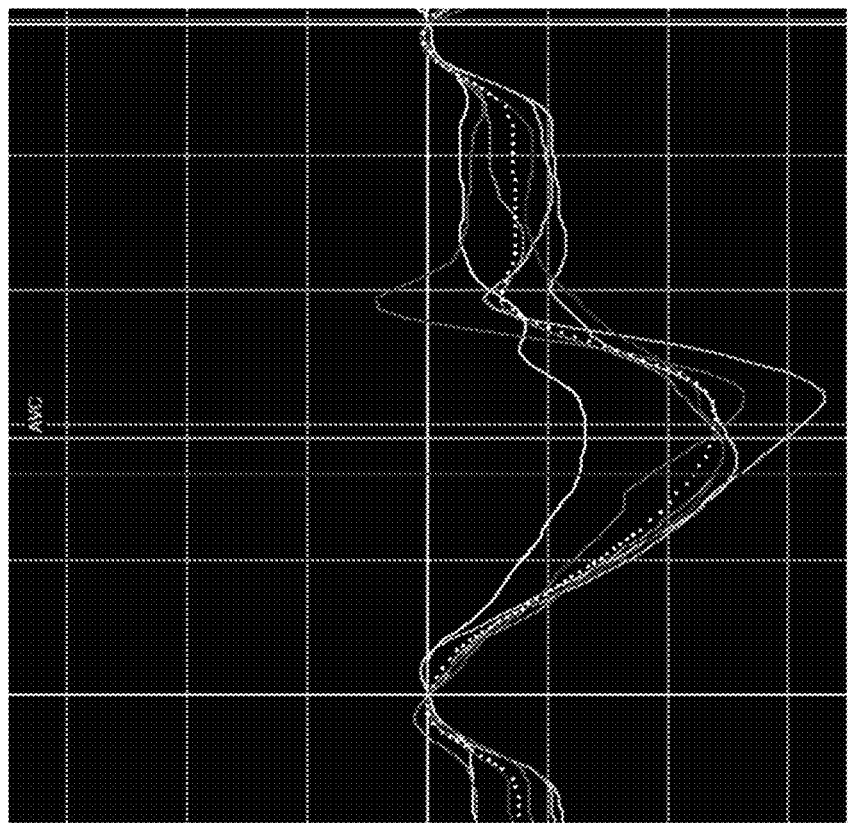
FIG. 3 depicts a spatio-temporal strain analysis graph which is analyzed by the system in accordance with an illustrative embodiment.
Figure 2:
FIG. 2 depicts a vertical scale bar that is used to obtain appropriate scaling values for a strain axis in accordance with an illustrative embodiment.
Figure 4:
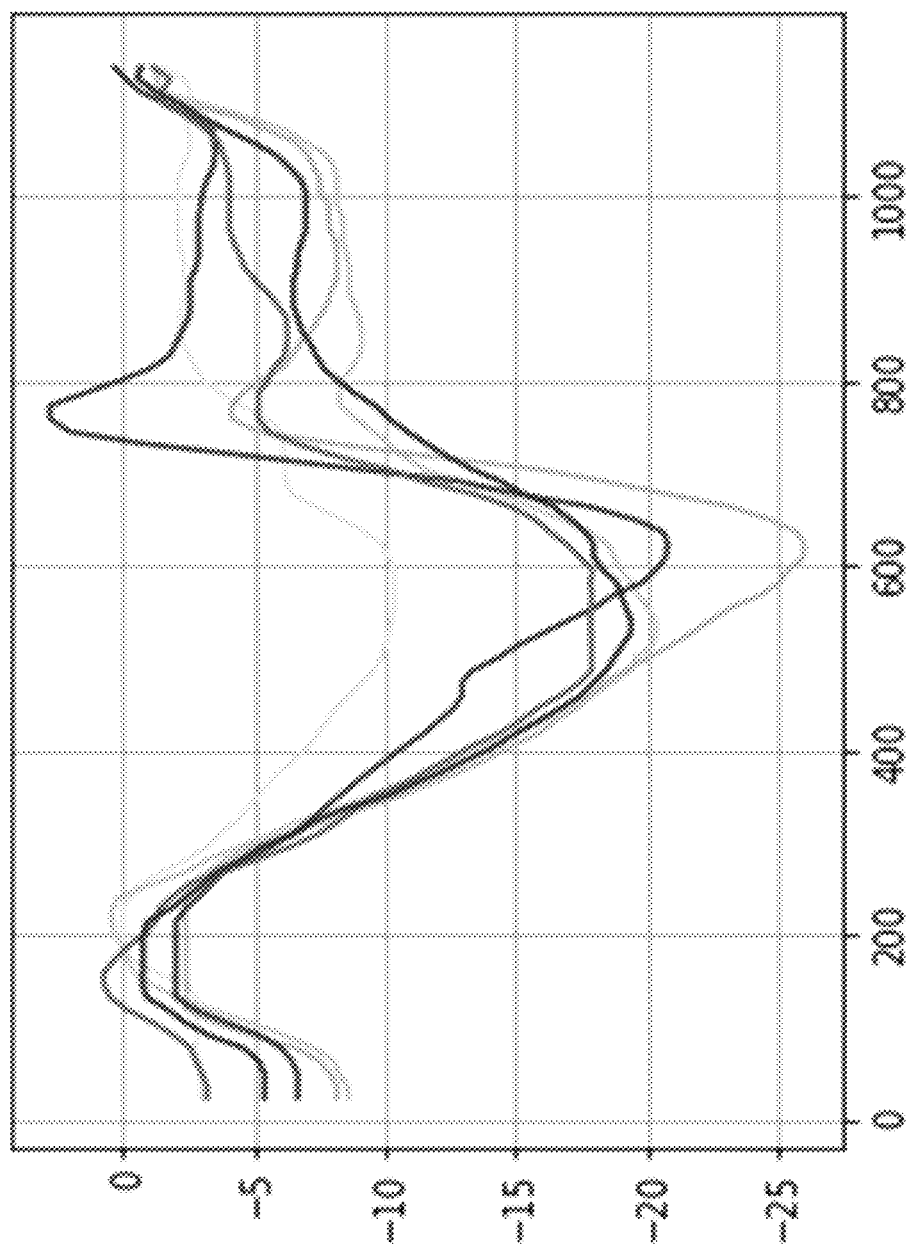
FIG. 4 depicts a final output graph in accordance with an illustrative embodiment.

In an illustrative embodiment, to perform data extraction, the picture of the strain output graph is ascertained, and the image is automatically segmented into 2 segments. The first segment contains a vertical scale bar, which is then analyzed with optical character recognition (OCR) to get the appropriate scaling values for the vertical or strain axis. FIG. 2 depicts a vertical scale bar that is used to obtain appropriate scaling values for a strain axis in accordance with an illustrative embodiment. The second segment contains the graph itself, which is converted to a 2D array of hue saturation values (HSV) for each pixel in the image. FIG. 3 depicts a spatio-temporal strain analysis graph which is analyzed by the system in accordance with an illustrative embodiment. By using preset vendor specific color profiles, all pixels within color bounds for a certain color are ascertained. Using these pixels' row and column index, they are turned into a point cluster (similar to a scatter gram). The points in the cluster are stitched together into one continuous line using an Interpolated Univariate Spline. Alternatively, a different stitching technique may be used. The interpolated curve can be stored as numerical values accurately scaled using the previously ascertained scale values, or can be output as another graph looking identical to the original. FIG. 4 depicts a final output graph in accordance with an illustrative embodiment.

Figure 5:
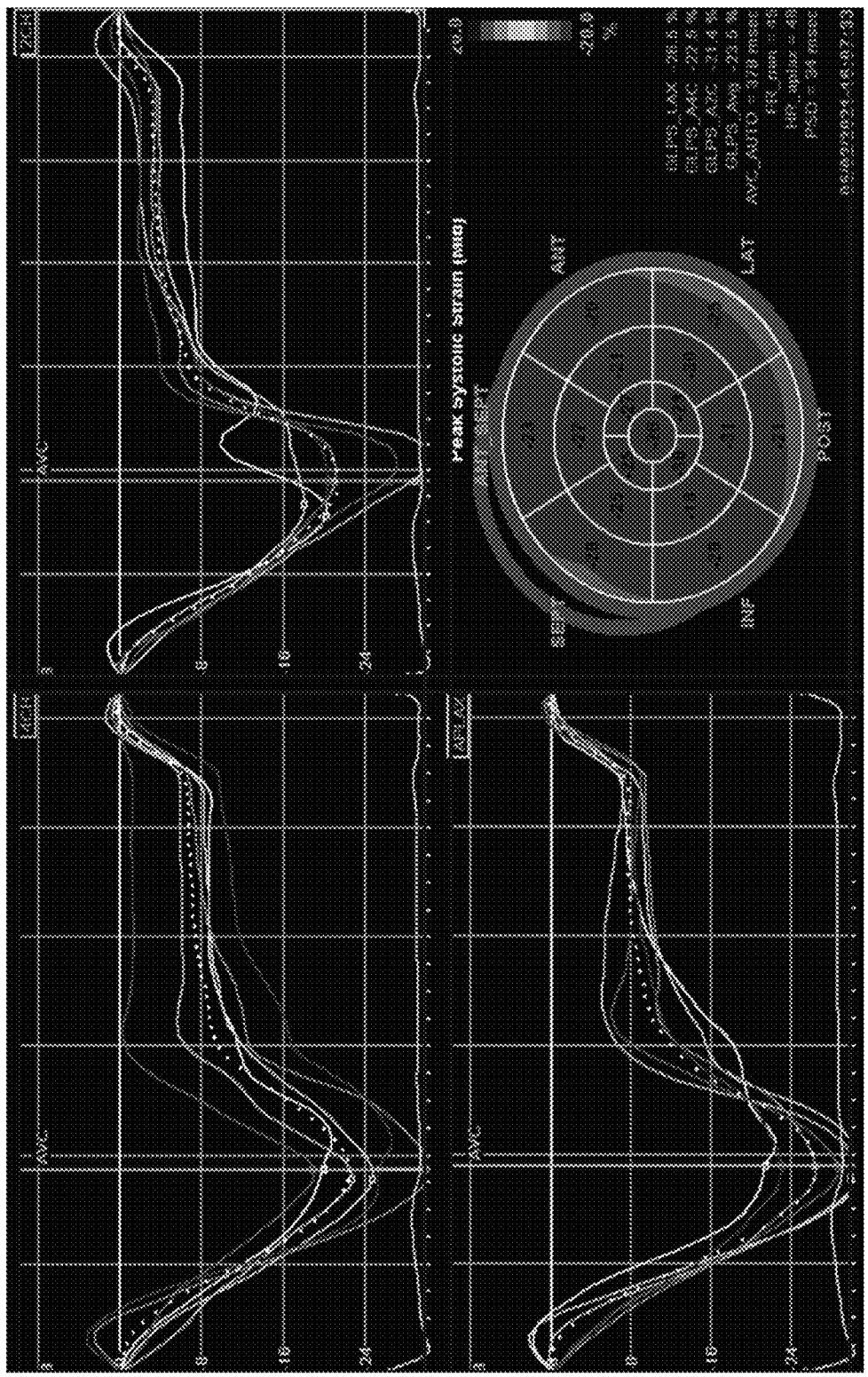
FIG. 5 depicts a complex strain data set having 18 curves distributed over 3 apical views in accordance with an illustrative embodiment.

While this approach has been validated for the most complex strain dataset (left ventricle, with 18 curves distributed over 3 apical views), it is equally applicable to the simpler datasets of the right ventricle and left and right atria. FIG. 5 depicts a complex strain data set having 18 curves distributed over 3 apical views in accordance with an illustrative embodiment. The proposed methods are also scalable and can be implemented on high-speed multi-core CPU-based computer clusters that are able to conduct the desired series of sequential transformations of the data, and can process thousands of graphs in short order, producing a rich set of data for the machine learning stage of the proposed system.

The raw numerical output of the strain graph extraction can be used as input into downstream artificial intelligence (AI) models typically used for high-throughput analysis of time-series data. Well-validated and emerging state-of-the-art machine learning methods for sequence analysis including deep neural networks with a self-attention mechanism (e.g. Transformer architectures), recurrent neural networks, and one-dimensional convolutional neural networks can be used to unlock hidden patterns in the data on a scale not previously possible. In an illustrative embodiment, the system can use both one-dimensional vectors derived from the strain curves themselves as input into these models, in addition to multimodal fusion architectures combining the derived strain curves with other structured (e.g., clinical features) and unstructured (e.g., raw imaging data, ECG waveforms) data via experimentation with feature concatenation at different levels in individual model architectures (e.g., early vs late fusion). Model assembling can also be performed. Transformer architectures in particular have proven effective in modeling multi-modal or mode agnostic datasets.

These models can be trained with the target of identifying novel clusters of strain patterns in an unsupervised fashion, with subsequent statistical analysis of these clusters to identify correlates to phenotypic disease and/or clinically meaningful patient outcomes in order to elucidate potential pathophysiologic mechanisms of disease. Additionally, supervised learning can be used to train the models to classify patients into certain disease phenotypes (e.g. cardiac amyloidosis, hypertrophic cardiomyopathy, hypertensive heart disease, familial dilated cardiomyopathies, arrhythmogenic right ventricular cardiomyopathy, and others) and predict patient outcomes, with the goal of developing intelligent systems which can be applied directly to strain curve information in a clinical workflow to aid in augmented diagnosis and prognostication in an end-to-end fashion. Weights for these deep learning models can be learned via backpropagation and gradient descent on the appropriate loss function for the particular task (e.g. clustering loss, binary cross-entropy loss, mean squared error, etc.).

Importantly, models can be trained on a subset of data that can be partitioned into training and validation datasets (to monitor for overfitting), and a separate hold-out subset of test data that the models will not be exposed to at all during the training process will be used to evaluate model performance. Ultimately, by using a variety of statistical methods and machine learning models, the proposed system is able to correlate the minutiae within strain curves to clinically relevant insights. As seen in other fields of medicine, such analysis has allowed for much progress in disease subtyping, AI based diagnosis, and tools to help clinicians and researchers.

Figure 6:
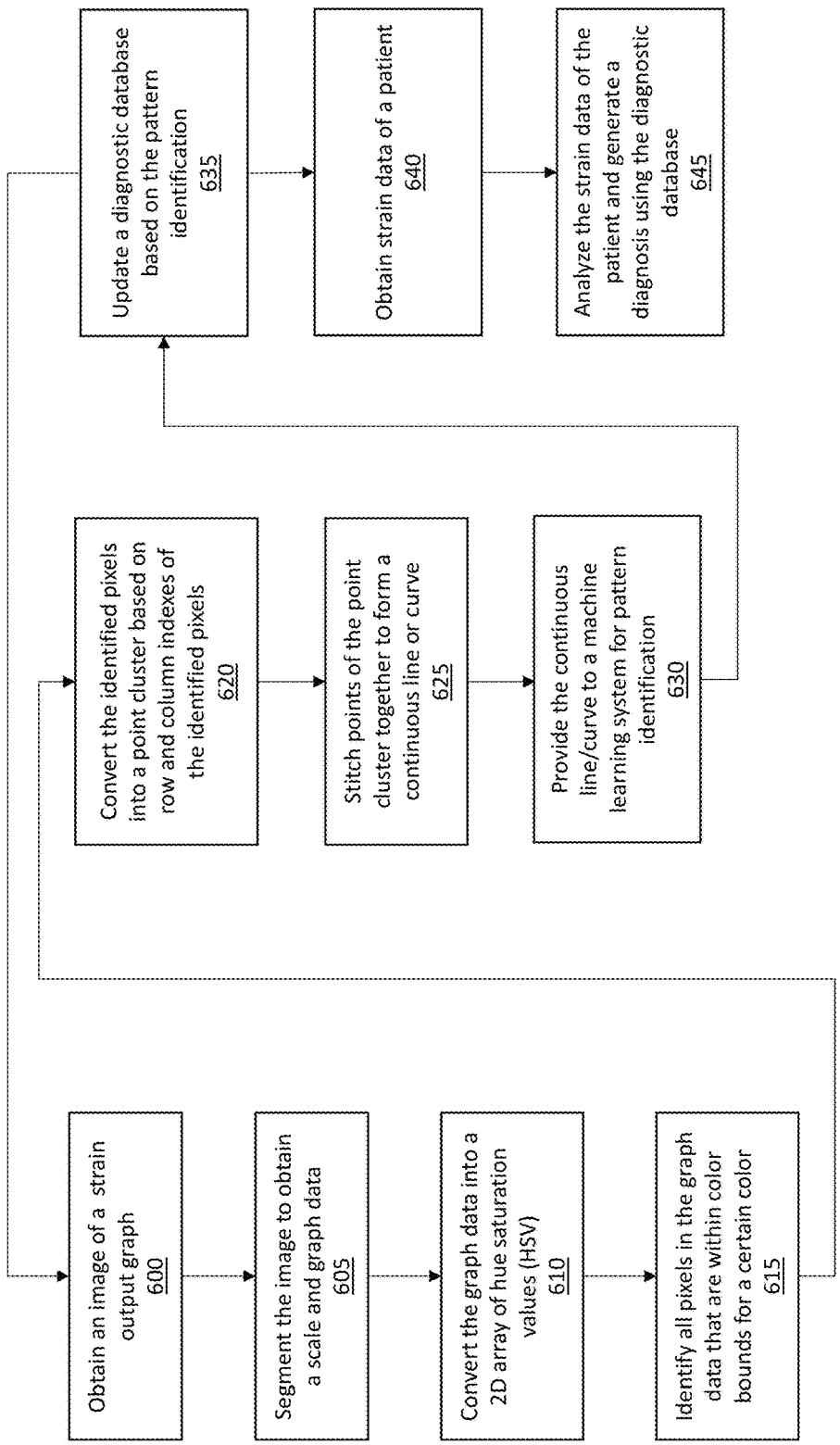
FIG. 6 is a flow diagram depicting operations to implement a strain image based diagnostic system in accordance with an illustrative embodiment.

FIG. 6 is a flow diagram depicting operations to implement a strain image based diagnostic system in accordance with an illustrative embodiment. In alternative embodiments, fewer, additional, and/or different operations may be performed. Also, the use of a flow diagram is not meant to limiting with respect to the order in which the operations are performed. In an illustrative embodiment, the operations of FIG. 6 can be performed by a computing system as described herein. In an operation 600, an image of a strain output graph is obtained. The image can be obtained automatically by a computing system that receives the image from a database or other storage repository. In an alternative embodiment, other data representing the strain results in addition to (or alternative to) the graph may also be received by the computing system.

In an operation 605, the image is segmented to obtain a scale and graph data. In an illustrative embodiment, the scale can be a vertical scale bar that can be analyzed using OCR and/or other techniques to obtain scaling values for the vertical or strain axis of the graph. The graph data refers to the various plots of strain curves that were present in the strain image. In an operation 610, the system converts the graph data into a two-dimensional array of hue saturation values (HSV) for each pixel in the image. In an operation 615, the system identifies all pixels in the graph data that are within color bounds for a certain color. In an illustrative embodiment, the color bounds are preset values that are vendor-specific to the strain test system used to obtain the image/data.

In an operation 620, the system converts the identified pixels into a point cluster based on row and column indexes of the identified pixels. In an operation 625, points of the point cluster are stitched together to form a continuous line or curve, using any stitching technique(s) known in the art. In an operation 630, the continuous line/curve is provided to a machine learning system for pattern identification. The machine learning system can include one or more deep neural networks with a self-attention mechanism (e.g. Transformer architectures), one or more recurrent neural networks, one or more one-dimensional convolutional neural networks, etc. The patterns can be based on timing data corresponding to identification of a peak strain, early systolic lengthening and post systolic shortening, myocardial stretch with atrial contraction, etc.

In an operation 635, a diagnostic database is updated based on the pattern identification. As indicated in FIG. 6, upon completion of the operation 635, the system continues to cycle through operations 600-635 to continue to update and improve the accuracy of the diagnostic database based on additional images of strain output graphs. In an illustrative embodiment, the diagnostic database, once created, is able to analyze new strain data and generate a diagnosis, outcome, etc. based on the stored patterns in the database. In an operation 640, strain data of a patient is obtained. In an operation 645, the strain data is analyzed and a diagnosis is generated using the diagnostic database. Specifically, the strain data of the patient is compared to the identified patterns in the diagnostic database. Upon identifying a match of the patient strain data to one or more of the identified patterns, the system is able to use the one or more identified patterns to generate a diagnosis for the patient.

Figure 7:
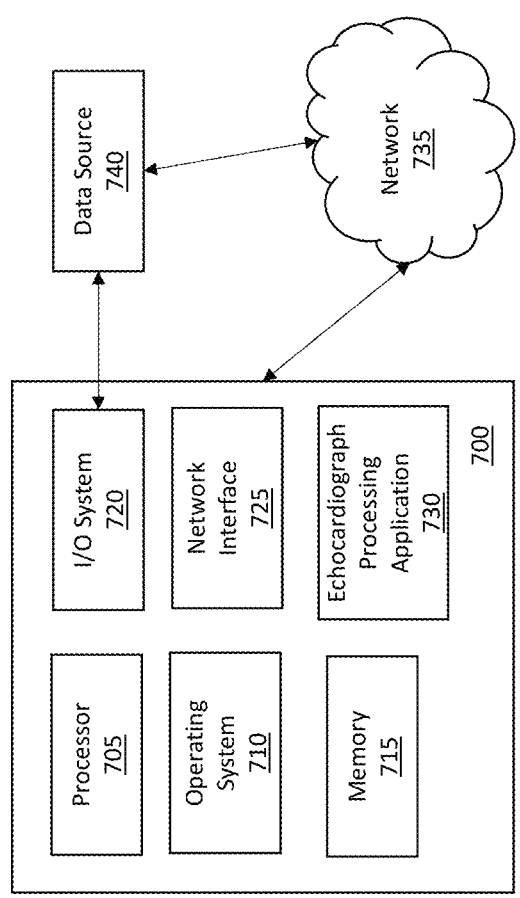
FIG. 7 is a block diagram of a computing system to implement the echocardiographic strain graph processing system in accordance with an illustrative embodiment.

Any of the methods described herein can be performed by a computing system that includes a processor, a memory, a user interface, transceiver, etc. Any of the operations described herein can be stored in the memory as computer-readable instructions. Upon execution of these computer-readable instructions by the processor, the computing system performs the operations described herein. As an example, FIG. 7 is a block diagram of a computing system to implement the echocardiographic strain graph processing system in accordance with an illustrative embodiment. The computing system 700 includes a data source 740 from which echocardiographic strain graphs are obtained, either directly or through a network 735. The data source 740 can be any type of database or other storage system in which the strain graphs are stored, a device/system that generates strain graphs, etc.

The computing system 700 includes a processor 705, an operating system 710, a memory 715, an input/output (I/O) system 720, a network interface 725, and an echocardiograph processing application 730. In alternative embodiments, the computing system 700 may include fewer, additional, and/or different components. The components of the computing system 700 communicate with one another via one or more buses or any other interconnect system. The computing system 700 can be any type of computing device (e.g., tablet, laptop, desktop, etc.) that has sufficient processing power to perform the operations described herein.

The processor 705 can be in electrical communication with and used to control any of the system components described herein. For example, the processor 705 can be used to execute the echocardiograph processing application 730, extract/receive strain graphs from the data source 740, segment the echocardiographic strain image data, analyze the segmented echocardiograph strain image data to generate a point cluster of pixels, stitch together points in the point cluster to generate a continuous curve that represents the echocardiographic strain image data, analyze the continuous curve, identify a heart condition, etc. The processor 705 can be any type of computer processor known in the art, and can include a plurality of processors and/or a plurality of processing cores. The processor 705 can include a controller, a microcontroller, an audio processor, a graphics processing unit, a hardware accelerator, a digital signal processor, etc. Additionally, the processor 705 may be implemented as a complex instruction set computer processor, a reduced instruction set computer processor, an x86 instruction set computer processor, etc. The processor 705 is used to run the operating system 710, which can be any type of operating system.

The operating system 710 is stored in the memory 715, which is also used to store programs, user data, pacemaker readings, network and communications data, peripheral component data, the echocardiograph processing application 730, and other operating instructions. The memory 715 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc. In some embodiments, at least a portion of the memory 715 can be in the cloud to provide cloud storage for the system. Similarly, in one embodiment, any of the computing components described herein (e.g., the processor 705, etc.) can be implemented in the cloud such that the system can be run and controlled through cloud computing.

The I/O system 720 is the framework which enables users and peripheral devices to interact with the computing system 700. The I/O system 720 can include a display, one or more speakers, one or more microphones, a keyboard, a mouse, one or more buttons or other controls, etc. that allow the user to interact with and control the computing system 700. The I/O system 720 also includes circuitry and a bus structure to interface with peripheral computing devices such as power sources, universal service bus (USB) devices, data acquisition cards, peripheral component interconnect express (PCIe) devices, serial advanced technology attachment (SATA) devices, high definition multimedia interface (HDMI) devices, proprietary connection devices, etc.

The network interface 725 includes transceiver circuitry (e.g., a transceiver that includes a transmitter and a receiver) that allows the computing system 700 to transmit and receive data to/from other devices such as the data source 740, other remote computing systems, servers, websites, etc. The network interface 725 enables communication through the network 735, which can be one or more communication networks. The network 735 can include a cable network, a fiber network, a cellular network, a wi-fi network, a landline telephone network, a microwave network, a satellite network, etc. The network interface 725 also includes circuitry to allow device-to-device communication such as Bluetooth® communication.

The echocardiograph processing application 730 can include software and algorithms in the form of computer-readable instructions which, upon execution by the processor 705, performs any of the various operations described herein such as receiving strain data, segmenting the strain data, analyzing the segmented data, converting the graph data to a 2D array of hue saturation values, identifying pixels in the strain data corresponding to a certain color, forming a point cluster of data values extracted from the strain data, stitching data points to form a curve, analyzing the curve to identify a pattern, updating a diagnostic database with the pattern information, identifying a heart condition based on strain data using the diagnostic database, transmitting diagnostic information, etc. The echocardiograph processing application 730 can utilize the processor 705 and/or the memory 715 as discussed above. In an alternative implementation, the echocardiograph processing application 730 can be remote or independent from the computing system 700, but in communication therewith.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A system to analyze heart data, the system comprising:
a memory configured to store echocardiographic strain image data; and
a processor operatively coupled to the memory and configured to:
segment the echocardiographic strain image data, wherein segmentation of the echocardiographic strain image data extracts a scale and graph data from the echocardiographic strain image data, wherein the processor is configured to convert the graph data into a two-dimensional array of hue saturation values;
analyze the segmented echocardiograph strain image data to generate a point cluster of pixels;
stitch together points in the point cluster to generate a continuous curve that represents at least a portion of the echocardiographic strain image data; and
analyze the continuous curve to identify a heart condition.

2. The system of claim 1, wherein the echocardiographic strain image data includes one or more visual graphs depicting a plurality of apical echo views of a heart.

3. The system of claim 2, wherein each of the apical echo views of the heart contain a plurality of curves that are coded to specify locations within the heart.

4. The system of claim 1, wherein the continuous curve is formed by use of an interpolated univariate spline on the point cluster.

5. The system of claim 1, wherein the processor is configured to identify all pixels in the graph data that represent a specific location of the heart.

6. The system of claim 5, wherein the processor is configured to convert the identified pixels into the point cluster of pixels.

7. The system of claim 6, wherein the point cluster is based on row and column indices of the identified pixels.

8. The system of claim 1, wherein the processor analyzes the continuous curve to identify one or more patterns present in the echocardiographic strain image data.

9. The system of claim 8, wherein the processor compares the one or more patterns to previously analyzed strain data to identify the heart condition.

10. The system of claim 8, wherein the one or more patterns relate to a timing of peak strain in the echocardiograph strain image data.

11. The system of claim 8, wherein the one or more patterns relate to early systolic lengthening and post systolic shortening.

12. The system of claim 8, wherein the one or more patterns relate to myocardial stretch with atrial contraction.

13. A method of analyzing heart data, the method comprising:
storing, in a memory, echocardiographic strain image data; and
segmenting, by a processor operatively coupled to the memory, the echocardiographic strain image data, wherein the segmenting includes segmenting the echocardiographic strain image data into a scale and graph data, and further comprising converting, by the processor, the graph data into a two-dimensional array of hue saturation values;

analyzing the segmented echocardiograph strain image data to generate a point cluster of pixels;

stitching together, by the processor, points in the point cluster to generate a continuous curve that represents at least a portion of the echocardiographic strain image data; and analyzing, by the processor, the continuous curve to identify a heart condition.

14. The method of claim 13, further comprising identifying, by the processor, all pixels in the graph data that represent a specific location of the heart, and converting the identified pixels into the point cluster of pixels.

15. The method of claim 13, further comprising analyzing, by the processor, the continuous curve to identify one or more patterns present in the echocardiographic strain image data.

16. The method of claim 15, further comprising comparing, by the processor, the one or more patterns to previously analyzed strain data to identify the heart condition.

* * * * *